US00PP26093P2

(12) United States Plant Patent
Tuchida

(10) Patent No.: US PP26,093 P2
(45) Date of Patent: Nov. 17, 2015

(54) ***ANEMONE* PLANT NAMED 'PRETTY LADY MARIA'**

(50) Latin Name: *Anemone hupehensis*
Varietal Denomination: Pretty Lady Maria

(71) Applicant: Hisashi Tuchida, Niigata (JP)

(72) Inventor: Hisashi Tuchida, Niigata (JP)

( * ) Notice: Subject to any disclaimer, the term of this patent is extended or adjusted under 35 U.S.C. 154(b) by 162 days.

(21) Appl. No.: 13/998,295

(22) Filed: Oct. 18, 2013

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Anemone* plant named 'Pretty Lady Maria', characterized by its upright and relatively compact plant habit; moderately vigorous growth habit; freely flowering habit; relatively large single type flowers that are white in color and positioned above the foliar plane; and good garden performance.

2 Drawing Sheets

Botanical designation: *Anemone hupehensis.*
Cultivar denomination: 'PRETTY LADY MARIA'.

BACKGROUND OF THE INVENTION

The present invention relates to a new and distinct cultivar of *Anemone*, botanically known as *Anemone hupehensis* and hereinafter referred to by the name 'Pretty Lady Maria'.

The new *Anemone* plant is a product of a planned breeding program conducted by the Inventor in Niigata, Japan. The objective of the breeding program is to create new uniform and freely-flowering *Anemone* plants with large flowers and attractive flower color.

The new *Anemone* plant originated from a cross-pollination in Niigata, Japan of *Anemone hupehensis* 'Alba', not patented, as the female, or seed, parent with an unnamed proprietary selection of *Anemone hupehensis*, not patented, as the male, or pollen, parent. The new *Anemone* plant was discovered and selected by the Inventor as a single flowering plant within the progeny of the stated cross-pollination in a controlled environment in Niigata, Japan in August, 2009.

Asexual reproduction of the new *Anemone* by root cuttings in a controlled environment in Niigata since October, 2009 has shown that the unique features of this new *Anemone* are stable and reproduced true to type in successive generations.

SUMMARY OF THE INVENTION

Plants of the new *Anemone* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'Pretty Lady Maria'. These characteristics in combination distinguish 'Pretty Lady Maria' as a new and distinct *Anemone* plant:

1. Upright and relatively compact plant habit.
2. Moderately vigorous growth habit.
3. Freely flowering habit.

4. Relatively large single type flowers that are white in color and positioned above the foliar plane.
5. Good garden performance.

Plants of the new *Anemone* can be compared to plants of the female parent. 'Alba'. Plants of the new *Anemone* differ primarily from plants of 'Alba' in plant height as plants of the new *Anemone* are taller than plants of 'Alba'.

Plants of the new *Anemone* can be compared to plants of the male parent selection. Plants of the new *Anemone* differ primarily from plants of the male parent selection in the following characteristics:

1. Plants of the new *Anemone* are shorter than plants of the male parent selection.
2. Plants of the new *Anemone* and the male parent selection differ in flower color as plants of the male parent selection have dark pink-colored flowers.

Plants of the new *Anemone* can be compared to plants of *Anemone hupehensis* 'Honorine Jobert', not patented. In side-by-side comparisons conducted in Hillegom, The Netherlands, plants of the new *Anemone* and 'Honorine Jobert' differed primarily in plant height as plants of the new *Anemone* were much shorter than plants of 'Honorine Jobert'.

Plants of the new *Anemone* can also be compared to plants of *Anemone hupehensis* 'Whirlwind', not patented. In side-by-side comparisons conducted in Hillegom, The Netherlands, plants of the new *Anemone* and 'Whirlwind' differed primarily in plant height as plants of the new *Anemone* were much shorter than plants of 'Whirlwind'. In addition, plants of the new *Anemone* had single type flowers whereas plants of 'Whirlwind' had semi-double to double type flowers.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet is a side perspective view of a typical plant of 'Pretty Lady Maria' in a ground bed in an outdoor nursery.

The photograph on the second sheet comprises a close-up view of a typical flowering plant of 'Pretty Lady Maria'.

DETAILED BOTANICAL DESCRIPTION

The aforementioned photographs and following observations, measurements and values describe plants grown in ground beds and 17-cm containers during the late summer in an outdoor nursery in Hillegom, The Netherlands and under cultural practices typical of commercial *Anemone* production. During the production of the plants, day temperatures ranged from 12° C. to 28° C. and night temperatures ranged from 4° C. to 14° C. Plants were one year old when the photographs and description were taken. In the following description, color references are made to The Royal Horticultural Society Colour Chart, 2007 Edition, except where general terms of ordinary dictionary significance are used.

Botanical classification: *Anemone hupehensis* 'Pretty Lady Maria'.

Parentage:

*Female, or seed, parent.*—*Anemone hupehensis* 'Alba', not patented.

*Male, or pollen, parent*.—Unnamed proprietary selection of *Anemone hupehensis*, not patented.

Propagation:

*Type*.—By in vitro propagation.

*Time to initiate roots, summer*.—About one week at temperatures of 20° C.

*Time to initiate roots, winter*.—About two weeks at temperatures of 20° C.

*Time to produce a rooted young plant, summer*.—About six to nine weeks at temperatures of 15° C. to 17° C.

*Time to produce a rooted young plant, winter*.—About nine to ten weeks at temperatures of 15° C. to 17° C.

*Root description*.—Fine, fibrous; light brown in color.

*Rooting habit*.—Freely branching; medium density.

Plant description:

*Plant and growth habit*.—Herbaceous perennial; upright and relatively compact plant habit with leaves and flowering stems developing from basal rosettes; about eleven basal branches develop per plant; moderately vigorous growth habit.

*Plant height*.—About 43.5 cm.

*Plant diameter*.—About 37.8 cm.

Branch description:

*Length*.—About 23.2 cm.

*Diameter*.—About 3 mm.

*Internode length*.—About 10.9 cm.

*Texture*.—Smooth, glabrous.

*Strength*.—Strong.

*Aspect*.—Erect to about 10° from vertical.

*Color*.—Close to 144A.

Leaf description:

*Arrangement*.—Alternate, compound, typically with three leaflets per leaf.

*Length, leaves*.—About 12.4 cm.

*Width, leaves*.—About 11.8 cm.

*Length, terminal leaflets*.—About 9.4 cm.

*Width, terminal leaflets*.—About 4.4 cm.

*Length, lateral leaflets*.—About 7.1 cm.

*Width, lateral leaflets*.—About 4.6 cm.

*Shape, leaves*.—Broadly ovate to deltoid in outline.

*Shape, terminal leaflets*.—Ovate.

*Shape, lateral leaflets*.—Roughly ovate.

*Apex, all leaflets*.—Acute.

*Base, terminal leaflets*.—Attenuate.

*Base, lateral leaflets*.—Attenuate, oblique.

*Margin, all leaflets*.—Serrate to biserrate.

*Texture, all leaflets, upper surface*.—Sparsely pubescent; rough.

*Texture, all leaflets, lower surface*.—Smooth, glabrous.

*Venation pattern, all leaflets*.—Palmate, laciniate.

*Color, all leaflets*.—Developing leaflets, upper surface: Close to 143A. Developing leaflets, lower surface: Close to 138B to 138C. Fully expanded leaflets, upper surface: Close to N137A to N137B and 146A; venation, close to 144A. Fully expanded leaflets, lower surface: Close to between 147B and 148B; venation, close to 144C.

*Leaf petioles*.—Length: About 7.6 cm. Diameter: About 2 mm. Texture, upper and lower surfaces: Smooth, glabrous. Color, upper and lower surfaces: Close to 144A.

*Terminal leaflet petioles*.—Length: About 1.6 cm. Diameter: About 1.5 mm. Texture, upper and lower surfaces: Smooth, glabrous. Color, upper and lower surfaces: Close to 144A.

*Lateral leaflet petioles*.—Length: About 6 mm. Diameter: About 1.5 mm. Texture, upper and lower surfaces: Smooth, glabrous. Color, upper and lower surfaces: Close to 144A.

Flower description:

*Flower arrangement and flowering habit*.—Single type rotate flowers arranged in compound cymes with strong peduncles that hold the flowers above the foliar plane; freely flowering habit with ten flowers per inflorescence; flowers face upright to outwardly.

*Fragrance*.—None detected.

*Natural flowering season*.—Plants of the new *Anemone* flower during the late summer in The Netherlands.

*Flower longevity*.—Individual flowers last about one week on the plant; flowers not persistent.

*Inflorescence height*.—About 17.9 cm.

*Inflorescence diameter*.—About 18.6 cm.

*Flower diameter*.—About 7.8 cm.

*Flower length (depth)*.—About 2.3 cm.

*Flower buds*.—Length: About 1.4 cm. Diameter: About 1.1 cm. Shape: Broadly ovate. Color: Close to 150B to 150C.

*Petals*.—Absent.

*Sepals*.—Quantity and arrangement: About five or six arranged in a single whorl. Length: About 3.4 cm. Width: About 2.5 cm. Shape: Broadly obovate to obovate. Apex: Rounded to retuse. Base: Acute. Margin: Entire. Texture, upper surface: Glabrous, smooth; velvety. Texture, lower surface: Densely pubescent; velvety. Color: When opening, upper surface: Close to NN155A; towards the base, close to 157D. When opening, lower surface: Close to 150D; towards the base, close to 150C. Fully opened, upper surface: Close to NN155D; with cooler temperatures, flushed with close to 69C to 69D. Fully opened, lower surface: Close to NN155C to NN155D; towards the base, close to 155A.

*Peduncles*.—Length: About 12.8 cm. Diameter: About 2 mm. Aspect: About 20° from vertical. Texture: Pubescent. Color: Close to 144A.

*Pedicels*.—Length: About 10.4 cm. Diameter: About 1.5 mm. Aspect: Erect to about 35° from the peduncle axis. Texture: Pubescent. Color: Close to 144A to 144B.

*Reproductive organs*.—Androecium: Stamen number per flower: About 240. Filament length: About 8 mm. Filament color: Close to NN155C to NN155D. Anther shape: Oblong to reniform. Anther length: About 2 mm. Anther color: Close to 17A. Amount of pollen: Scarce. Pollen color: Close to 15C. Gynoecium: Pistil number per flower: About 200. Pistil length: About 1 mm. Stigma shape: Club-shaped. Stigma color: Close to 145A. Style length: About 0.5 mm. Style color: Close to 144A to 144B. Ovary color: Close to 145A. Seeds and fruits: Seed and fruit development have not been observed on plants of the new *Anemone*.

Garden performance: Plants of the new *Anemone* have been observed to have good garden performance, to tolerate high temperatures of about 35° C. and to be hardy to USDA Hardiness Zone 4.

Pathogen & pest resistance: Plants of the new *Anemone* have not been observed to be resistant to pests and pathogens common to *Anemone* plants.

It is claimed:

1. A new and distinct *Anemone* plant named 'Pretty Lady Maria' as illustrated and described.

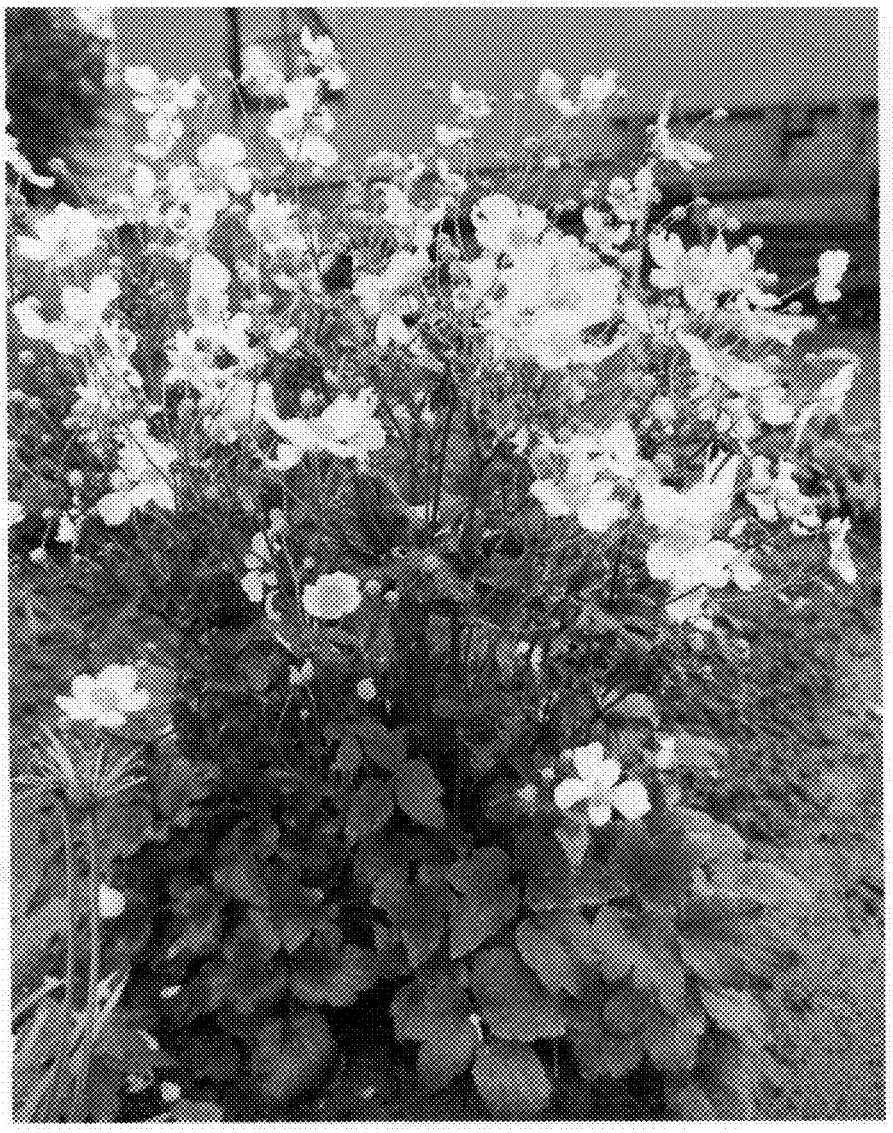

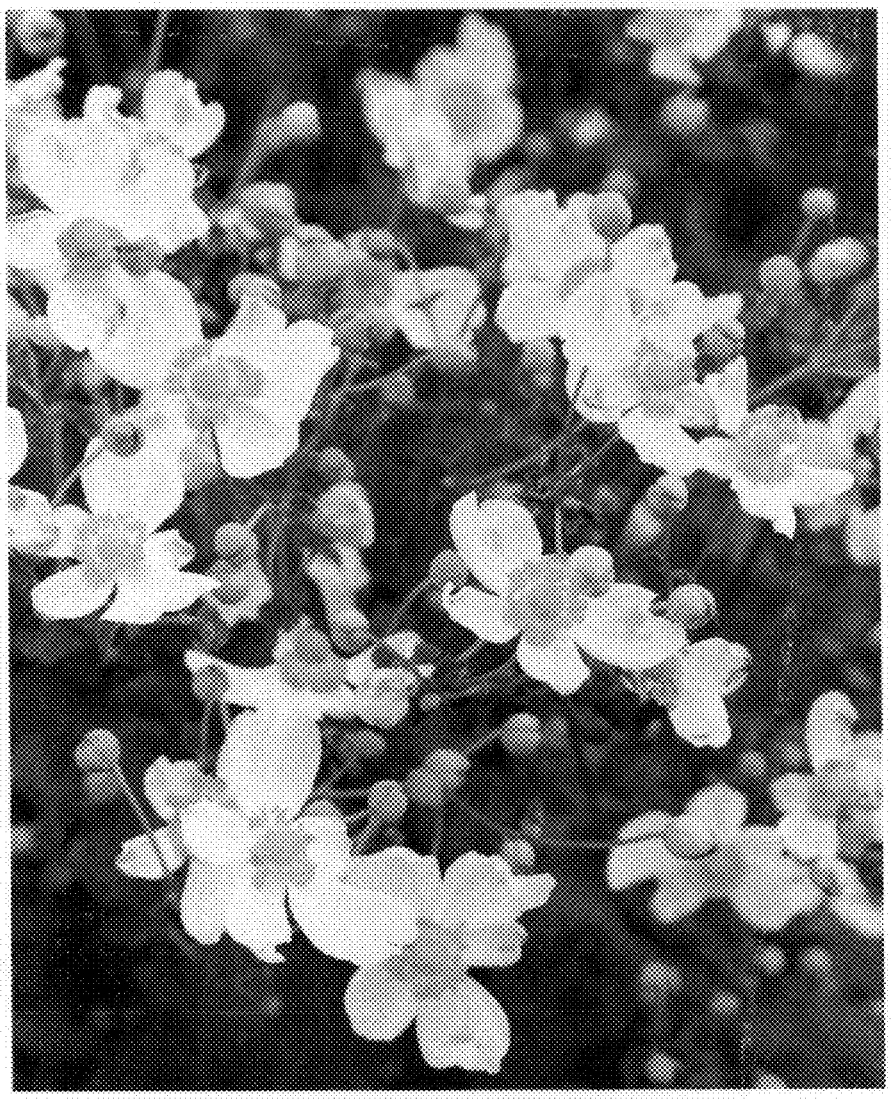

* * * * *